(12) United States Patent
Shiota et al.

(10) Patent No.: US 6,925,148 B2
(45) Date of Patent: Aug. 2, 2005

(54) X-RAY FLUOROSCOPIC APPARATUS

(75) Inventors: Tadahiro Shiota, Kyoto (JP); Masayuki Kamegawa, Nara (JP)

(73) Assignee: Shimadzu Corporation, Kyoto (JP)

( * ) Notice: Subject to any disclaimer, the term of this patent is extended or adjusted under 35 U.S.C. 154(b) by 108 days.

(21) Appl. No.: 10/689,904

(22) Filed: Oct. 21, 2003

(65) Prior Publication Data

US 2004/0096029 A1 May 20, 2004

(30) Foreign Application Priority Data

Nov. 1, 2002 (JP) ........................ 2002-320229

(51) Int. Cl.[7] ............................ H05G 1/30; H05G 1/02
(52) U.S. Cl. ............................ 378/91; 378/42; 378/55; 378/189; 378/190; 378/205; 378/208
(58) Field of Search ............................ 378/42, 55, 91, 378/146, 167, 177, 189, 190, 196, 197, 205, 207, 208, 209

(56) References Cited

U.S. PATENT DOCUMENTS 4,024,403 A * 5/1977 Bernstein et al. ........... 378/177
5,493,594 A * 2/1996 Hamada et al. ............. 378/34
6,155,713 A * 12/2000 Watanabe .................... 378/197
6,325,537 B1 * 12/2001 Watanabe .................... 378/197

FOREIGN PATENT DOCUMENTS

JP     2001-249086      9/2001

* cited by examiner

Primary Examiner—Allen C. Ho
(74) Attorney, Agent, or Firm—Rankin, Hill, Porter & Clark LLP

(57) ABSTRACT

X- and y-axis moving mechanisms are provided for positioning a sample table in the x-axis and the y-axis directions. A yT-axis moving mechanism for moving those moving mechanisms in a direction along a tilting direction of a X-ray camera is provided separately from the x- and y-axes moving mechanisms. When the X-ray camera is tilted, the sample table is moved by the yt axis moving mechanism and a z-axis moving mechanism, whereby a viewpoint of the sample and a fluoroscopic magnification factor set before the X-ray camera is tilted are left unchanged. The coordinates on the sample table by the moving mechanisms before the X-ray camera is tilted can be used as they are even after the camera is tilted.

4 Claims, 3 Drawing Sheets

X-RAY FLUOROSCOPIC APPARATUS

BACKGROUND OF THE INVENTION

1. Field of the Invention

The present invention relates to an X-ray fluoroscopic inspection apparatus. More particularly, the invention relates to an X-ray fluoroscopic apparatus which is applicable to an apparatus for displaying a fluoroscopic image of an object to be fluoroscoped on a monitor screen or radiographic fluoroscopic image, and also to an X-ray CT apparatus for constructing a CT image from the fluoroscopic image.

2. Description of the Related Art

In the X-ray fluoroscopic apparatus, such as an industrial X-ray fluoroscopic inspection apparatus, an X-ray camera containing an image intensifier, a CCD camera and the like is disposed in opposition to an X-ray source. An object (referred to as a sample), such as a sample, is located between the CCD camera and the X-ray source. The X-ray camera radiographs an X-ray fluoroscopic image of the sample.

Normally, a sample table is disposed between the X-ray source and the X-ray camera. The sample table positions the sample so that a desired viewpoint on the sample is located within a visual field of the X-ray camera. The sample table is movable in two axes (x-axis and y-axis), perpendicular to each other, on a plane along a surface of the table. The sample table is rotatable about a z-axis perpendicular to the x- and y-axis, viz., extending in an optical axis of the X-rays emitted from the X-ray source.

This kind of X-ray fluoroscopic apparatus is equipped with a mechanism which moves the X-ray camera and the sample table in an optical axis (z-axis) direction of the X-rays emitted from the X-ray source so as to vary a magnification factor of the fluoroscopic image as desired. Some type of the X-ray fluoroscopic apparatus is further equipped with a mechanism which tilts the X-ray camera in a predetermined direction with respect to the optical axis of the X-ray source so as to enable the camera to fluoroscope the object at an inclination angle.

The X-ray fluoroscopic apparatus with the tilting mechanism involves the following problem. An operator places a sample on the sample table, and positions the sample table so as to have a desired viewpoint on the sample in a state that the X-ray camera is positioned on the optical axis of the X-ray, for example. Then, the operator tilts the X-ray camera to fluoroscope the sample at the inclination angle. At this time, the viewpoint on the sample moves within the visual field or moves out of the visual field, disadvantageously. In this case, even if the sample table is moved in the x-axis or the y-axis direction so that the viewpoint falls within the visual field of the X-ray camera, a distance (SOD) between the X-ray source and the sample at the position of the table before the camera is tilted will change from the original distance. Therefore, even if a distance (SID) between the X-ray source and the X-ray detector is fixed, a fluoroscopic magnification factor represented by SID/SOD changes from its value before the camera is tilted.

In a case where a rotating mechanism for rotating the sample table is put on the mechanism for moving the table in the x-axis and the y-axis directions, the following problem arises. When the sample is put on the sample table and the viewpoint on the sample is positioned so as to be located at the center of a visual field of the camera, and the table are rotated, the viewpoint is sometimes greatly shifted from the center of the visual field of the X-ray camera since the rotary shaft of the sample table has been moved in the x-axis and the y-axis directions. In such a case, when the sample table is rotated, the viewpoint moves out of the visual field while describing an arc.

There is known a technique to solve that problem (see JP-A-2001-249086 (pp 3 to 12)). In the technique, the correction amounts of the movement of the sample table in the x-axis and the y-axis directions are successively computed so as to keep the original position of the viewpoint within the visual field when the X-ray camera is tilted or the sample table is rotated. The moving mechanism for the x- and y-axis direction movements is driven by using the computing results.

Where this technique is used, the viewpoint always stays within the visual field of the X-ray camera even if the X-ray camera is tilted or the sample table is positioned and rotated. In particular, an efficiency of the work of fluoroscoping the sample at high magnification factor is considerably improved.

The above-mentioned related-art tracking technique has the following disadvantage. A set of x and y coordinates of the position on the table at which the operator first sets the sample will change in x and y directions by quantities of the movement-amount correction after the camera is titled or the table is rotated. This makes it difficult for the operator to use values of the x and y coordinates as the reference for fluoroscopic visual field position on the sample.

SUMMARY OF THE INVENTION

For the above background reasons, a first object of the present invention is to provide an X-ray fluoroscopic apparatus which keeps an original position of the viewpoint of the sample within the visual field of the X-ray camera and an original fluoroscopic magnification factor when the X-ray camera is tilted, and further, keeps the X and Y coordinates of a desired position within a visual field of the X-ray camera at which the operator sets a viewpoint of the sample before the X-ray camera is tilted, and hence, allows the coordinates to be used after the camera is tilted.

A second object of the present invention is to provide an X-ray fluoroscopic apparatus in which even when the sample table is moved in the z-axis direction in a state that the X-ray camera is tilted, the original position of the viewpoint of the sample within the visual field of the X-ray camera is kept unchanged, and also in this case, the original X and Y coordinates are kept unchanged and may be used after the sample table is moved.

To achieve the first object, there is provided a first X-ray fluoroscopic apparatus comprising:

an X-ray source;

an X-ray camera located at a position on which X-rays emitted from the X-ray source are incident;

a sample table, located between the X-ray source and the X-ray camera, for supporting a sample;

a tilting mechanism for tilting the X-ray camera to a given tilting direction;

a positioning moving mechanism for moving the sample table in x- and y-axes, orthogonal to each other, on a plane along a surface of the sample table in order to position a sample to be within a visual field of the X-ray camera;

a rotating mechanism for rotating the sample table together with the positioning moving mechanism about a z-axis extending in directions in which the sample table moves to and from the X-ray source, the z-axis being orthogonal to the x-axis and the y-axis;

a position correction moving mechanism for moving the sample table together with the rotating mechanism and the positioning moving mechanism in the tilting direction of the X-ray camera;

a z-axis moving mechanism for moving the sample table together with the position correction moving mechanism, the rotating mechanism and the positioning moving mechanism in the z-axis direction; and a tilting tracing mechanism for driving the correction moving mechanism and the z-axis moving mechanism according to a tilting angle of the X-ray camera while not driving the positioning moving mechanism, when the X-ray camera is tilted by the tilting mechanism, so that a viewpoint of the sample and a fluoroscopic magnification factor before the X-ray camera is tilted can be kept.

To achieve the second object, there is provided a second X-ray fluoroscopic apparatus comprising:

an X-ray source;

an X-ray camera located at a position on which X-rays emitted from the X-ray source are incident;

a sample table, located between the X-ray source and the X-ray camera, for supporting a sample;

a tilting mechanism for tilting the X-ray camera to a given tilting direction;

a positioning moving mechanism for moving the sample table in x- and y-axes, orthogonal to each other, on a plane along a surface of the sample table in order to position a sample to be within a visual field of the X-ray camera;

a rotating mechanism for rotating the sample table together with the positioning moving mechanism about a z-axis extending in directions in which the sample table moves to and from the X-ray source, the z-axis being orthogonal to the x-axis and the y-axis;

a position correction moving mechanism for moving the sample table together with the rotating mechanism and the positioning moving mechanism in the tilting direction of the X-ray camera;

a z-axis moving mechanism for moving the sample table together with the position correction moving mechanism, the rotating mechanism and the positioning moving mechanism in the z-axis direction; and an in-changing-magnification-factor tracing mechanism for driving the correction moving mechanism according to a movement amount of the sample table in the z-axis direction while not driving the positioning moving mechanism, when the sample table is moved in the z-axis direction in a state that X-rays are tilted by the tilting mechanism, so that a viewpoint of the sample before the movement of the sample table in the z-axis can be kept.

In the invention, the dedicated moving mechanism is provided separately from the positioning moving mechanism for moving the sample table in the x-axis and the y-axis directions. The dedicated moving mechanism corrects a position of the sample table when the X-ray camera is tilted or when the sample table is moved in the z-axis direction in a state that the X-ray camera is tilted. The dedicated moving mechanism is provided closer to the base side (when the respective mechanisms are vertically arranged, it is located under the positioning moving mechanism. The base side will be referred to as "lower side", and a side opposite to the base side will be referred to as "upper side") than the positioning moving mechanism. The rotating mechanism for the sample table is disposed under the positioning moving mechanism for moving the table in the x-axis and the y-axis directions and above the dedicated moving mechanism exclusively operated for the correction. Further, the z-axis moving mechanism is provided for moving all the mechanisms in the z-axis.

In the first X-ray fluoroscopic apparatus, the viewpoint and the fluoroscopic magnification factor, which are before the camera is tilted are kept as they are in a manner that when the X-ray camera is tilted by the tilting mechanism, the positioning moving mechanism for moving the table in the x-axis and the y-axis directions is not driven, but the correction moving mechanism, located thereunder, for moving the sample table in a tilting direction of the camera and the z-axis moving mechanism, are driven. The coordinates on the sample table which are set by the positioning moving mechanism at the time of camera tilting are left fixed. Accordingly, the original coordinates which keep the viewpoint and the fluoroscopic magnification factor, may be continuously used.

In the second X-ray fluoroscopic apparatus, when the sample table is moved in the z-axis direction in a state that the X-ray camera is tilted by the tilting mechanism, the correction moving mechanism is driven according to an amount of movement of the table in the z-axis direction, whereby the viewpoint of the sample set before its movement in the z-axis is kept. Also in this case, the original coordinates of the sample table remain unchanged, and hence, may be used as they are.

In those X-ray fluoroscopic apparatus, the table rotating mechanism is located under the positioning moving mechanism. Accordingly, even when the sample table is moved in the x-axis and the y-axis directions by the positioning moving mechanism, the positional relation between the X-ray camera and the rotary shaft of the sample table remains unchanged. Accordingly, it is possible to prevent the viewpoint from moving out of the visual field of the X-ray camera.

DETAILED DESCRIPTION OF THE INVENTION

Figure 1:
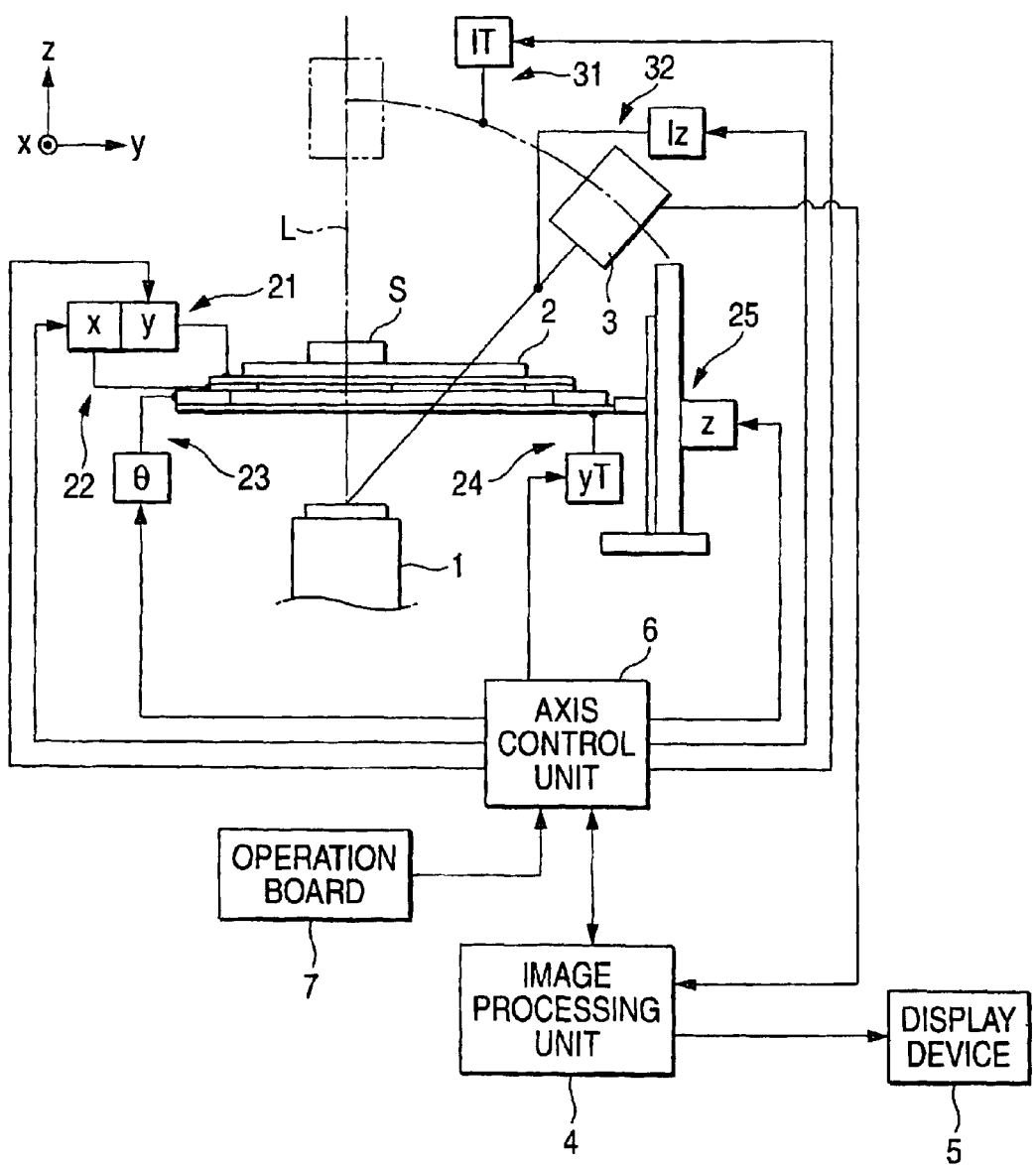
FIG. 1 shows an arrangement of an embodiment of the present invention which contains a mechanical arrangement shown in model form and an electrical arrangement shown in block form.

The preferred embodiments of the present invention will be described with reference to the accompanying drawings. FIG. 1 shows an arrangement of an embodiment of the present invention which contains a mechanical arrangement shown in model form and an electrical arrangement shown in block form.

An X-ray source 1 formed with an X-ray tube is disposed such that an optical axis L of X-rays (=center axis of X-rays irradiated) is oriented in a vertical direction (z-axis direction). A sample table 2 having a surface expanding in a horizontal plane (x-y plane) is disposed above the X-ray source 1. Further, an X-ray camera 3 is disposed above the sample table 2, while being spaced from each other by a predetermined distance.

The X-ray camera 3 may be tilted, by a tilting mechanism 31, to a desired angle about an axis (lT axis) extending along the x-axis as the center axis with a focal point of the X-ray source 1 as the center position, viz., on a z-y plane. The X-ray camera 3 may be moved at a desired tilting angle in directions (lz-axis directions) in which the camera moves to and from the X-ray source 1, by a camera moving mechanism 32.

The sample table 2 is movable in the x-axis and the y-axis directions, orthogonal to each other, on a horizontal plane when an operator operates a y-axis moving mechanism 21 and an x-axis moving mechanism 22 which are provided under the sample table 2 on an operation board 7 described later on. The y-axis moving mechanism 21 and the x-axis moving mechanism 22 cooperate to form a positioning mechanism for positioning a sample S within a visual field of the X-ray camera 3.

A rotating mechanism 23 is disposed under the y-axis moving mechanism 21 and the x-axis moving mechanism 22. The rotating mechanism 23 rotates the sample table 2 about an axis (=θ axis) along the z-axis. When the rotating mechanism 23 is driven, the sample table 2 is rotated about the θ axis, together with the y-axis moving mechanism 21 and the x-axis moving mechanism 22.

A yT-axis moving mechanism 24 to be described later is disposed under the rotating mechanism 23. The yT-axis moving mechanism 24 corrects a position of the sample table 2. When the y T-axis moving mechanism 24 is driven, the respective members located above the yT-axis moving mechanism 24, viz., the sample table 2, the y-axis moving mechanism 21, the x-axis moving mechanism 22, and the rotating mechanism 23, can be all moved in the y-axis direction, which is along the tilting direction in which the X-ray camera 3 is tilted by the camera tilting mechanism 31.

When a z-axis moving mechanism 25 is driven, the sample table 2 and all of the moving mechanisms are moved in the z-axis directions in which those are moved to and from the X-ray source 1.

A sample S as an object to be fluoroscoped is placed on the sample table 2, and an underside of the sample is irradiated with X-rays. The X-rays transmitted through the sample S are incident on the X-ray camera 3. The X-ray camera 3 consists of, for example, a combination of an image intensifier and a CCD camera, which is known. Instantaneous output images from the X-ray camera 3 are successively fed to the image processing unit 4, and then a fluoroscopic image of the sample S is displayed by the display device 5.

Motors as drive sources for the y-axis moving mechanism 21, the x-axis moving mechanism 22, the rotating mechanism 23, the yT-axis moving mechanism 24, the z-axis moving mechanism 25, the tilting mechanism 31 and the camera moving mechanism 32 are all under control of control signals output from an axis control unit 6. The axis control unit 6 mainly contains a CPU and its peripheral devices, and is connected to the operation board 7 by which an operator enters various commands into the X-ray fluoroscopic apparatus. The operator operates the operation board 7 to drive the mechanisms other than the yT-axis moving mechanism 24 to move the sample table 2 and the X-ray camera 3 as desired.

The axis control unit 6 includes a memory for storing a current position of the sample table 2 or the X-ray camera 3 when it is driven by each mechanism, and contains a visual field/magnification factor keeping program installed there into. When the X-ray camera 3 is tilted, or when the sample table 2 is moved in the z-axis direction during the X-ray camera 3 being titled, the sample table automatically moves, under control of the program, to thereby keep the visual field and/or the magnification factor, which are originally set.

Figure 2:
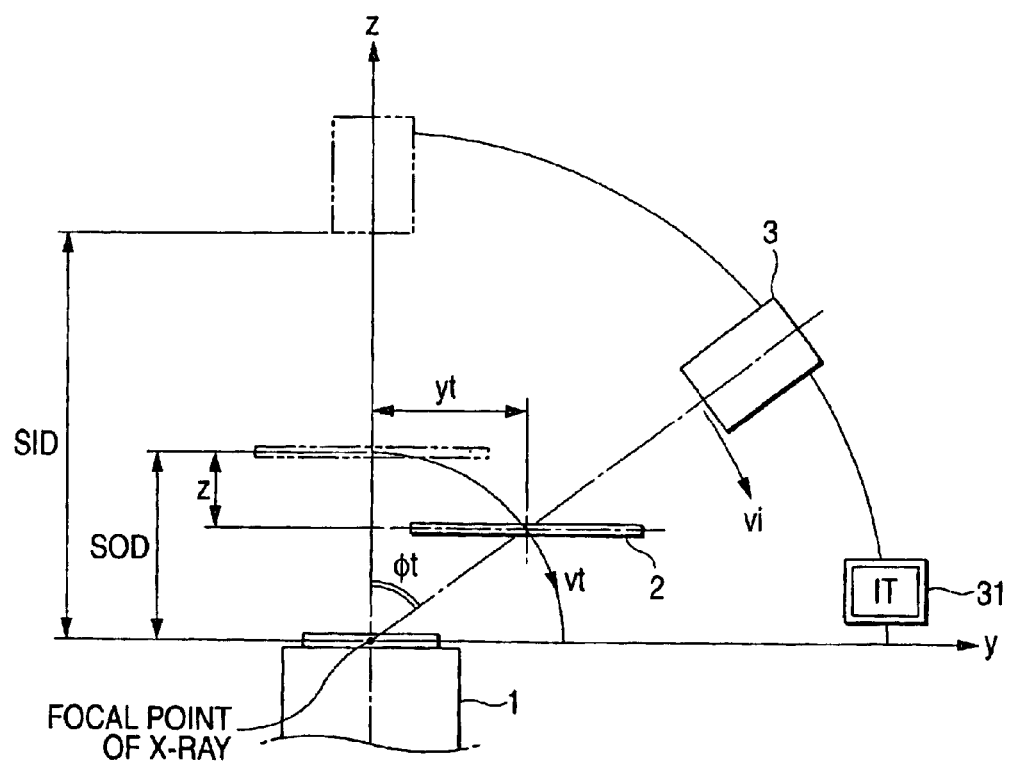
FIG. 2 is a diagram useful in explaining operation of the X-ray fluoroscopic apparatus when an X-ray camera is tilted in the embodiment.

Firstly, operation of the X-ray fluoroscopic apparatus when the X-ray camera 3 is tilted will be described with reference to FIG. 2. When the operator operates the operation board 7 to enter a drive command into the tilting mechanism 31, the axis control unit 6 drives the tilting mechanism 31 to tilt the X-ray camera 3. At the same time, the axis control unit 6 drives the yT-axis moving mechanism 24 and the z-axis moving mechanism 25, which are provided for the sample table 2, to operate those mechanisms in the following ways. Therefore, those mechanisms trace the tilting operation of the X-ray camera 3 to thereby keep the visual field and the fluoroscopic magnification factor, which are originally set before the X-ray camera is tilted.

It is assumed that a distance between the X-ray source 1 (=focal point. The same shall apply hereinafter.) and the X-ray camera 3 when a tilting command is issued, is SID, and a distance between the X-ray source 1 and the sample table 2 under the same condition is SOD. It is supposed that the sample table 2 is arcuately moved in synchronism with the tilting operation of the X-ray camera 3. Then, a moving speed "vt" of the sample table 2 is computed by the following equation (1)

$$vt = \omega \cdot SOD \quad (1)$$

when the X-ray camera 3 tilts at a speed "vi", and an angular velocity is ω (vi=ω SID).

To realize an arcuate movement of the sample table by use of the yT-axis moving mechanism 24 and the z-axis moving mechanism 25, a moving speed "vyt" of the yT-axis moving mechanism 24 and a moving speed "vz" of the z-axis moving mechanism 25 are computed by using the following equations (2) and (3).

$$vyt = vt \cdot \cos \phi t = \omega \cos \phi t \cdot SOD \quad (2)$$

$$vz = vt \cdot \sin \phi t = \omega \sin \phi t \cdot SOD \quad (3)$$

where ωt=instantaneous tilting angle.

A movement amount "yt" of the sample table in the y-axis direction and a movement amount "z" of the same in the z-axis are given by $$yt = SOD \sin \phi t \quad (4)$$

$$z = SOD(1 - \cos \phi t) \quad (5)$$

When the operator operates the operation board 7 to issue a command to tilt the X-ray camera 3 to an angle φt, the tilting mechanism 31 operates in response to the tilting command. At the same time, the yT-axis moving mechanism 24 and the z-axis moving mechanism 25 automatically operate in accordance with the angle φt and the angular velocity ω. Therefore, the sample table 2 moves at the moving speed "vyt" in the y-axis direction, by the movement amount "yt", and moves at the moving speed "vz" in the z-axis direction, by the movement amount "z". The tilting mechanism 31, the yT-axis moving mechanism 24 and the z-axis moving mechanism 25 are collectively managed and controlled by the axis control unit 6. While the operator operates the operation board 7 to drive the tilting mechanism 31, the yT-axis moving mechanism 24 and the z-axis moving mechanism 25 operate as mentioned above. Therefore, in the X-rays fluoroscopic image displayed by the display device 5, only a fluoroscoping direction progressively changes, while the center of the visual field and the fluoroscoping magnification factor remain unchanged.

To correct the position of the sample table 2 as mentioned above, the y-axis moving mechanism 21 is never driven, so that the x and y coordinates on the sample table 2 that is operated by the operator before the X-ray camera is operated are left unchanged. Accordingly, the operator can position the sample table 2 by using the coordinate values after the X-ray camera is tilted.

To automatically correct the position of the sample table 2 in order to keep the viewpoint of the sample and the fluorescent magnification factor, which are originally set, at the time of tilting the X-ray camera 3, the SOD is used for the distance from the X-ray source 1 to the sample table 2 in the computation mentioned above. To keep more accurately the viewpoint and the fluorescent magnification factor, which are originally set, a distance from the X-ray source 1 to a marked part on the sample S, viz., a true SOD, is used in place of the SOD used in the computation already described. However, the distance from the X-ray source 1 to the marked position on the sample S is not known exactly. Accordingly, the true SOD is obtained in the following manner, and it is automatically obtained.

In a state that an X-rays fluoroscopic image is displayed by the display device 5, the marked part is specified on the image. Then, in this state, the sample table 2 is moved by a distance $\Delta$ in the x-axis or y-axis direction, and thus, the marked part within the sample S also moves by the distance $\Delta$ and the marked part on the screen also moves. A ratio of a movement amount $\sigma$ of the marked part on the screen to the distance $\Delta$ represents a fluoroscopic magnification factor on a plane on which the marked part lies. Therefore, a fluoroscopic magnification factor P of the marked part can accurately be computed in the following manner. That is, a program is prepared by using the image processing technique such that when a tilting command is issued, the sample table 2 is moved, for example, in the x-axis direction so that the marked part moves by the distance $\sigma$ on the screen and is moved back to the original position. A movement amount $\Delta$ of the sample table 2 at that time is also detected.

The distance SID from the X-ray source 1 to the X-ray detector 3 can be exactly known since a position of the X-ray camera 3 in the z direction caused by the apparatus constant and the camera moving mechanism 32 is already known. Therefore, the true SOD can be exactly computed by using the following equation (6).

$$\text{True } SOD = SID/P \quad (6)$$

When the thus computed SOD is applied to the equations (1) to (5), the X-ray camera 3 can be tilted, while keeping the viewpoint and the fluoroscopic magnification factor in extremely exact level.

A computing method utilizing a correlation function describing a correlation between image information before and after the image is moved may be used for computing a movement amount of the marked part on the screen.

Operation of the X-ray fluoroscopic apparatus when the sample table 2 is moved up and down in the z-axis in a state that the X-ray camera 3 is tilted to a given angle $\phi$ with respect to the optical axis L of X-rays, will be described with reference to FIG. 3.

When the operator operates the operation board 7 in a state that the X-ray camera 3 is tilted to issue a command to move the sample table 2 in the z-axis by the z-axis moving mechanism 25, the axis control unit 6 responds to the command and drives the z-axis moving mechanism 25. At the same time, the axis control unit 6 automatically drives the yT-axis moving mechanism 24 to keep the viewpoint.

Figure 3:
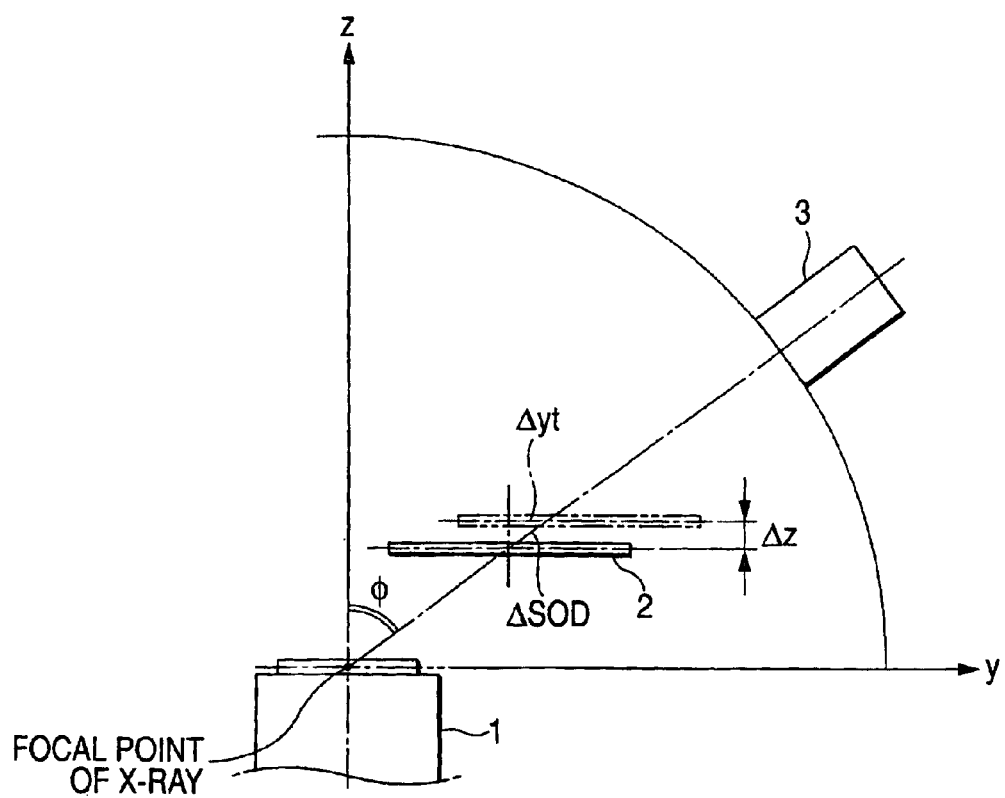
FIG. 3 is a diagram useful in explaining operation of the X-ray fluoroscopic apparatus when a sample table is moved in the z-axis direction in a state that the X-ray camera is tilted, in the embodiment.

Specifically, the viewpoint before the sample table is moved in the z-axis direction can be kept by moving the sample table 2 by a distance $\Delta yt$ in they-axis in FIG. 3 where a movement amount of the sample table 2 is $\Delta z$ by the z-axis moving mechanism 25. The distance $\Delta yt$ can be computed by using the following equations (7) and (8). In the figure, $$\Delta SOD = \Delta z/\cos \phi \quad (7),$$

then, we have $$\Delta yt = \Delta z (\sin \phi/\cos \phi) = \Delta z \cdot \tan \phi \quad (8)$$

Accordingly, the viewpoint before the movement in the z-axis is kept in a manner that when the operator operates the operation board 7 in a state that the X-ray camera 3 is tilted, to thereby move the sample table 2 in the z-axis, the yT-axis moving mechanism 24 is automatically moved by a distance $\Delta yt$ according to its movement amount $\Delta z$. With this function, even when the sample table 2 is moved in the z-axis in order to change the magnification factor in a state that the X-ray camera 3 is tilted, the center of the visual field of the X-ray camera 3 does not change, and only the magnification factor of the fluoroscopic image is changed.

According to the vertical position relation among the moving mechanisms for the sample table 2 in the instant embodiment, the rotating mechanism 23 is located under the y-axis moving mechanism 21 and the x-axis moving mechanism 22, and it rotates the sample table 2 together with both the y-axis moving mechanism 21 and the x-axis moving mechanism 22. Therefore, even if the rotating mechanism 23 is rotated after the operation board 7 is operated to drive the y-axis moving mechanism 21 and the x-axis moving mechanism 22 to thereby fix the visual field of the X-ray camera 3, the position relation between the X-ray camera 3 and the rotating mechanism 23 is left unchanged. This fact brings about an advantage that the visual field is not changed irrespective of the mechanism rotation.

In the embodiment mentioned above, the optical axis L of X-rays is oriented in the vertical direction, and the moving mechanisms and the rotating mechanism, which are for the sample table 2, are vertically arranged. Alternatively, the optical axis L of X-rays is oriented in the horizontal direction, and the moving mechanisms and the rotating mechanism, which are for the sample table 2, are laterally (horizontally) arranged.

As seen from the foregoing description, the viewpoint and the fluoroscopic magnification factor of the X-ray camera which are set before the X-ray camera is tilted are kept as they by automatically driving a dedicated moving mechanism, which is provided separately from a moving mechanism for moving the sample table in the x-axis and the y-axis directions, and a z-axis moving mechanism, when the X-ray camera is tilted. With this feature, there is no need of operator's adjustment of viewpoint and the fluoroscopic magnification factor when the X-ray camera is tilted. Further, the coordinates determined by driving the moving mechanism for the positioning the table in the x-axis and the y-axis directions before the X-ray camera is tilted can be used as they are even after the X-ray camera is tilted.

Also in the invention, when the sample table is moved in the z-axis in a state that the X-ray camera is tilted to a desired angle, the viewpoint of the sample is kept at its position set before the sample table is moved in the z-axis direction by automatically moving the dedicated moving mechanism provided separately from the moving mechanism for moving the sample table in the x-axis and the y-axis direction. Therefore, any adjustment of the viewpoint of the sample is not required for the operator even if he/she moves the sample table in the z-axis with the intention of changing the fluoroscopic magnification factor in a state that the camera is tilted. Also in this case, the coordinates on the sample table that are determined by driving the moving mechanism for the positioning the table in the x-axis and the y-axis directions before the sample table is moved in the z-axis, can be used as they are even after the table is moved.

What is claimed is:

1. An X-ray fluoroscopic apparatus comprising:

an X-ray source;

an X-ray camera located at a position on which X-rays emitted from said X-ray source are incident;

a sample table, located between said X-ray source and said X-ray camera, for supporting a sample;

a tilting mechanism for tilting said X-ray camera to a given tilting direction;

a positioning moving mechanism for moving said sample table in x- and y-axes, orthogonal to each other, on a plane along a surface of said sample table in order to position a sample to be within a visual field of said X-ray camera;

a rotating mechanism for rotating said sample table together with said positioning moving mechanism about a z-axis extending in directions in which said sample table moves to and from said X-ray source, said z-axis being orthogonal to said x-axis and said y-axis;

a position correction moving mechanism for moving said sample table together with said rotating mechanism and said positioning moving mechanism in the tilting direction of said X-ray camera;

a z-axis moving mechanism for moving said sample table together with said position correction moving mechanism, said rotating mechanism and said positioning moving mechanism in the z-axis direction; and a tilting tracing mechanism for driving said correction moving mechanism and said z-axis moving mechanism according to a tilting angle of said X-ray camera while not driving said positioning moving mechanism, when said X-ray camera is tilted by said tilting mechanism, so that a viewpoint of the sample and a fluoroscopic magnification factor before said x-ray camera is tilted can be kept.

2. The X-ray fluoroscopic apparatus according to claim 1, wherein said tilting tracing mechanism calculates a moving speed and a movement amount of said position correction moving mechanism and a moving speed and a movement amount of said z-axis moving mechanism based on the titling angle of said x-ray camera, and said tilting tracing mechanism drives said position correction moving mechanism and said z-axis moving mechanism so that they moves with respective calculated moving speeds and movement amounts.

3. An X-ray fluoroscopic apparatus comprising:

an X-ray source;

an X-ray camera located at a position on which X-rays emitted from said X-ray source are incident;

a sample table, located between said X-ray source and said X-ray camera, for supporting a sample;

a tilting mechanism for tilting said X-ray camera to a given tilting direction;

a positioning moving mechanism for moving said sample table in x- and y-axes, orthogonal to each other, on a plane along a surface of said sample table in order to position a sample to be within a visual field of said X-ray camera;

a rotating mechanism for rotating said sample table together with said positioning moving mechanism about a z-axis extending in directions in which said sample table moves to and from said X-ray source, said z-axis being orthogonal to said x-axis and said y-axis;

a position correction moving mechanism for moving said sample table together with said rotating mechanism and said positioning moving mechanism in the tilting direction of said X-ray camera;

a z-axis moving mechanism for moving said sample table together with said position correction moving mechanism, said rotating mechanism and said positioning moving mechanism in the z-axis direction; and an in-changing-magnification-factor tracing mechanism for driving said correction moving mechanism according to a movement amount of said sample table in the z-axis direction while not driving said positioning moving mechanism, when said sample table is moved in the z-axis direction in a state that said x-ray camera is tilted by said tilting mechanism, so that a viewpoint of the sample before said movement of said sample table in the z-axis can be kept.

4. The X-ray fluoroscopic apparatus according to claim 3, wherein said in-changing-magnification-factor tracing mechanism calculates a movement distance of said correction moving mechanism based on the movement amount of said sample table in the z-axis direction, and drives said correction moving mechanism so that it moves by the calculated movement distance.

* * * * *